(12) United States Patent
Parisot et al.

(10) Patent No.: US 7,371,395 B2
(45) Date of Patent: May 13, 2008

(54) VACCINE FORMULATIONS

(75) Inventors: Alexis Guy Andre Parisot, Lyons (FR); Stephanie Marie-Catherine Desgouilles-Blechet, Lyons (FR); Catherine Charreyre, Saint-Laurent de Mure (FR)

(73) Assignee: Merial Limited, Duluth, GA (US)

( * ) Notice: Subject to any disclaimer, the term of this patent is extended or adjusted under 35 U.S.C. 154(b) by 462 days.

(21) Appl. No.: 10/899,181

(22) Filed: Jul. 26, 2004

(65) Prior Publication Data
US 2005/0079185 A1    Apr. 14, 2005

Related U.S. Application Data

(60) Provisional application No. 60/490,345, filed on Jul. 24, 2003.

(51) Int. Cl.
*A61K 39/39* (2006.01)
*A61K 51/00* (2006.01)
*A61K 39/12* (2006.01)
*A61K 45/00* (2006.01)
*A61K 9/107* (2006.01)

(52) U.S. Cl. ............................ 424/283.1; 424/204.1; 424/278.1

(58) Field of Classification Search ............... None
See application file for complete search history.

(56) References Cited

U.S. PATENT DOCUMENTS 6,500,662 B1 * 12/2002 Calvert et al. ............ 435/235.1
6,660,272 B2 * 12/2003 Allan et al. ............... 424/204.1
6,943,152 B1 * 9/2005 Audonnet et al. ............ 514/44
2002/0025986 A1 * 2/2002 Rodham et al. ............... 516/98

FOREIGN PATENT DOCUMENTS

| EP | 1095662 A1 | 5/2001 |
| FR | 1562758 A | 4/1969 |
| FR | 2824269 A1 | 11/2002 |
| WO | WO9956776 A2 | 11/1999 |
| WO | WO02074283 A1 | 9/2002 |

OTHER PUBLICATIONS

Zelenay, et al. Immunostimulatory effects of plasmid DNA and synthetic oligodeoxynucleotides. Eur. J. Immunol. 2003; 33:1382-1392.*
Gizurarson S, Jonsdottir VM, Heron I. Intranasal administration of diphtheria toxoid. Selecting antibody isotypes using formulations having various lipophilic characteristics. Vaccine. May 1995;13(7):617-21.

(Continued)

*Primary Examiner*—Mary E. Mosher
*Assistant Examiner*—Stuart W. Snyder
(74) *Attorney, Agent, or Firm*—Judy Jarecki-Black; Merial Limited; Thomas Kowalski

(57) ABSTRACT

The present invention provides for a novel oil-in-water (O/W) emulsion, with increased stability in the presence of bacterial or viral suspensions, especially those concentrated and non-purified or weakly purified. The emulsion of the present invention can act as vehicle for the delivery of a pharmaceutical composition comprising at least one immunogen and, in particular, an immunogen selected from the group comprising an inactivated pathogen, an attenuated pathogen, a subunit, a recombinant expression vector, and a plasmid or combinations thereof.

29 Claims, 4 Drawing Sheets

OTHER PUBLICATIONS

Lee JM, Park KM, Lim SJ, Lee MK, Kim CK. Microemulsion formulation of clonixic acid: solubility enhancement and pain reduction. J Pharm Pharmacol. Jan. 2002;54(1):43-9.

Edelman, "An Update on Vaccine Adjuvants in Clinical Trial," Aids Research and Human Retroviruses 8(8):1409-1411 (1992).

McElrath, "Selection of potent immunological adjuvants for vaccine construction," seminars in Cancer Biology 6:375-385 (1995).

Aucouturier et al., "Adjuvants designed for veterinary and human vaccines," Vaccine 19:2666-2672 (2001).

East et al., "Adjuvants for New Veterinary Vaccines," Chapter 1 in Progress in Vaccinology, vol. 4 Veterinary Vaccines, Springer Verlag, NY 1993, pp. 1-28.

Altman et al., "Immunomodifiers in Vaccines," Advances In Veterinary Science and Comparative Medicine 33:301-343 (1989).

Wiilson et al., "Tissue Reaction and Immunity in Swine Immunized with *Actinobacillus pleuropneumoniae* Vaccines," Can J Vet Res 59:299-305 (1995).

\* cited by examiner

Lung Lesion Score (max 28)

VACCINE FORMULATIONS

This application claims priority to U.S. Provisional App. No. 60/490,345 filed 24 Jul. 2003, the contents of which is incorporated by reference in its entirety.

FIELD OF THE INVENTION

The present invention relates to oil-in-water emulsions, their use as adjuvants, and pharmaceutical, immunologic, or vaccine compositions comprising the same.

DESCRIPTION OF THE RELATED ARTS

The use of adjuvants in vaccines is well known. An adjuvant is a compound that, when combined with a vaccine antigen, increases the immune response to the vaccine antigen as compared to the response induced by the vaccine antigen alone. Among strategies that promote antigen immunogenicity are those that render vaccine antigens particulate, those that polymerize or emulsify vaccine antigens, methods of encapsulating vaccine antigens, ways of increasing host innate cytokine responses, and methods that target vaccine antigens to antigen presenting cells (Nossal, 1999, In: *Fundamental Immunology*. Paul (Ed.), Lippincott-Raven Publishers, Philadelphia, Pa.; Vogel and Powell, 1995, In: *Vaccine Design*. The Subunit and Adjuvant Approach. Powell and Newman (Eds.), Plenum Press, NY, N.Y. p. 141). Because of the essential role adjuvants play in improving the immunogenicity of vaccine antigens, the use of adjuvants in the formulation of vaccines has been virtually ubiquitous (Nossal, 1999, supra; Vogel and Powell, 1995, supra; see also PCT publication WO 97/18837, the teachings of which are incorporated herein by reference). Conventional adjuvants, well-known in the art, are diverse in nature. They may, for example, consist of water-insoluble inorganic salts, liposomes, micelles or emulsions, i.e. Freund's adjuvant. Other adjuvants may be found in Vogel and Powell, 1995, mentioned supra. Although there is no single mechanism of adjuvant action, an essential characteristic is their ability to significantly increase the immune response to a vaccine antigen as compared to the response induced by the vaccine antigen alone (Nossal, 1999, supra; Vogel and Powell, 1995, supra). In this regard, some adjuvants are more effective at augmenting humoral immune responses; other adjuvants are more effective at increasing cell-mediated immune responses (Vogel and Powell, 1995, supra); and yet another group of adjuvants increase both humoral and cell-mediated immune responses against vaccine antigens (Vogel and Powell, 1995, supra).

Generally, emulsions used in vaccine formulation comprise a mixture of oil, aqueous solution and surfactants. Some emulsions incorporate a lipophilic surfactant such as Span 80® and a hydrophilic surfactant such as Tween 80®. These emulsions may also contain compounds such as lecithin or saponin known to have ionic surfactant properties.

However, problems of stability can be observed with emulsions used as vaccine adjuvants, in particular during storage or transport. This is particularly true when these compositions contain concentrated immunogens, especially non-purified concentrated immunogens. Typically, this is the case with adjuvants used in inactivated (killed) vaccines. This problem is even more significant with multivalent vaccine compositions because the immunogens are more concentrated in the same volume of diluent.

Another problem with adjuvant use is linked to a risk of adverse events such as toxicity or local inflammation at the site of injection. For example, a local inflammatory response and/or granulomae may result after injection. In order to limit such an adverse reaction, surfactants and other components in the emulsion may be reduced; however, the reduction may then result in a decrease in the stability of the vaccine composition. There is, therefore, a need for novel adjuvants and vaccine compositions containing such adjuvants with increased safety and stability.

SUMMARY OF THE INVENTION

In a first embodiment the present invention provides for a novel oil-in-water (O/W) emulsion, with increased stability in the presence of bacterial or viral suspensions, especially those concentrated and non-purified or weakly purified.

Another embodiment of the present invention provides for a stable, safe and easily administrable, in particular injectable, O/W emulsion acting as a vehicle for the delivery of a pharmaceutical composition comprising at least one active ingredient that may be, more particularly, an immunogen.

Yet another embodiment of the present invention provides for a stable, safe and injectable O/W emulsion acting as an adjuvant to increase the immune response induced by an immunogen. In particular, the present invention provides a novel adjuvant which, when used in a vaccine composition containing an immunogen increases the vaccinate's cellular immune response, humoral immune response or, preferably, both to the immunogen.

Yet another embodiment of the present invention provides a stable, safe and immunogenic composition or vaccine comprising an O/W emulsion.

A further embodiment of the present invention provides for a method of making a vaccine composition using the adjuvant of the instant invention; the vaccine composition so obtained; and methods of using thereof.

Still another embodiment of the present invention provides for a kit comprising an immunogen or other pharmaceutical product in a first vial, and an adjuvant made according to the present invention in a second vial, with the adjuvant designed to be mixed with the immunogen or other vaccine product before use.

In one preferred embodiment, the present invention provides for an injectable oil-in-water (O/W) emulsion comprising:
(1) an aqueous solution containing an immunogen;
(2) a mineral oil;
(3) a non-ionic lipophilic surfactant;
(4) a non-ionic hydrophilic surfactant having a low HLB value which comprises ethoxylated fatty acid diesters of sorbitan (generally having HLB value between 11 and 13).

In another preferred embodiment, the present invention provides for an injectable oil-in-water (O/W) emulsion comprising:
(1) an aqueous solution containing an immunogen;
(2) a non-ionic hydrophilic surfactant having a high hydrophilic-lipophilic balance (HLB) value greater than 13 and less than 40, in particular HLB$\geq$13.5, and preferably HLB$\geq$14;
(3) a mineral oil;
(4) a non-ionic lipophilic surfactant;
(5) a non-ionic hydrophilic surfactant having a low HLB value (HLB value of about 9 to about 13).

In yet another preferred embodiment, the present invention provides for a vaccine composition comprising a novel emulsion containing at least one immunogen suitable for eliciting an immunologic response in a vaccinate. The invention further provides such compositions wherein the emulsion acts as an adjuvant to increase the immune response induced by the immunogen, in particular, to increase the cellular response, the humoral response or preferably both.

In another preferred embodiment the present invention provides for a method of making a vaccine composition wherein an immunogen, especially an immunogen in lyophilized form or in an aqueous solution, is mixed with the adjuvant according to the instant invention. The immunogen may be selected from the group consisting of: inactivated pathogens, attenuated pathogens, sub-unit antigens, recombinant expression vectors including plasmids, and the like. The pathogen may be bacterial, viral, protozoal, or fungal in origin or the immunogen may constitute an antitoxin.

In another preferred embodiment, the present invention provides for a method of inducing an immune response in a vaccinate against a pathogen comprising administering the vaccine composition of the present invention to the vaccinate.

In another preferred embodiment, the present invention provides for kits comprising at least two vials, in a first vial an immunogen, especially an immunogen in lyophilized form or in solution in an aqueous medium, and in a second vial an adjuvant or emulsion according to the present invention.

It is noted that in this disclosure and particularly in the claims, terms such as "comprises", "comprised", "comprising" and the like can have the meaning attributed to such terms in U.S. patent law; e.g., they can mean "includes", "included", "including", and the like; and that terms such as "consisting essentially of" and "consists essentially of" have the meaning ascribed to them by U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein.

DETAILED DESCRIPTION OF THE INVENTION

Figure 1:
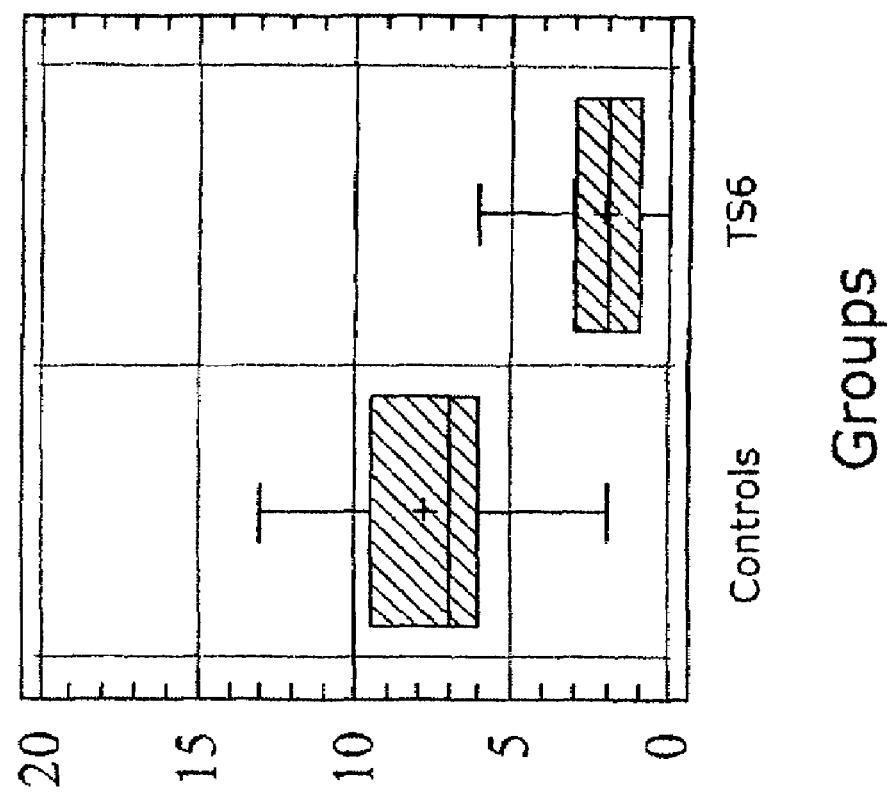
FIG. 1 illustrates lung lesion scores of piglets challenged 28 days after vaccination according to example 3. The mean value is shown by a cross, the lower quartile and the upper quartile by a box, the statistical median by a horizontal line in the box, the minimum to the maximum value by a vertical line.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents. The contents of all references, published patents, and patents cited throughout the present application are hereby incorporated by reference in their entirety.

For convenience, certain terms employed in the Specification, Examples, and appended claims are collected here.

As used herein, the term "animal" includes all vertebrate animals including humans. It also includes an individual animal in all stages of development, including embryonic and fetal stages. In particular, the term "vertebrate animal" includes, but not limited to, humans, canines (e.g., dogs), felines (e.g., cats); equines (e.g., horses), bovines (e.g., cattle) porcine (e.g., pigs), as well as in avians. The term "avian" as used herein refers to any species or subspecies of the taxonomic class ava, such as, but not limited to, chickens (breeders, broilers and layers), turkeys, ducks, a goose, a quail, pheasants, parrots, finches, hawks, crows and ratites including ostrich, emu and cassowary.

As used herein, the term "pig" or "piglet" means an animal of porcine origin, while "sow" refers to a female of reproductive age and capability.

As used herein, the term "virulent" means an isolate that retains its ability to be infectious in an animal host.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with thimerosal or formalin), sonication, radiation, heat or any other convention means sufficient to prevent replication or growth of the organism while maintaining its immunogenicity.

As used herein, the term "immunogenicity" means capable of producing an immune response in a host animal against an antigen or antigens. This immune response forms the basis of the protective immunity elicited by a vaccine against a specific infectious organism.

As used herein, the term "immune response" refers to a response elicited in an animal. An immune response may refer to cellular immunity (CMI); humoral immunity or may involve both. The present invention also contemplates a response limited to a part of the immune system. For example, a vaccine composition of the present invention may specifically induce an increased gamma interferon response.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

As used herein, the term "multivalent" means a vaccine containing more than one antigen whether from the same species (i.e., different isolates of *Mycoplasma hyopneumonia*), from a different species (i.e., isolates from both *Pasteurella hemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

As used herein, the term "adjuvant" means a substance added to a vaccine to increase a vaccine's immunogenicity. The mechanism of how an adjuvant operates is not entirely known. Some adjuvants are believed to enhance the immune response by slowly releasing the antigen, while other adjuvants are strongly immunogenic in their own right and are believed to function synergistically. Known vaccine adjuvants include, but are not limited to, oil and water emulsions (for example, complete Freund's adjuvant and incomplete Freund's adjuvant), *Corynebacterium parvum*, Bacillus Calmette Guerin, aluminum hydroxide, glucan, dextran sulfate, iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N,N-dioctadecyl-N',N'-bis(2-hydroxyethyl)-propanediamine), paraffin oil, muramyl dipeptide and the like.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

The present invention provides a novel oil-in-water (O/W) adjuvant or emulsion comprising:
(1) an aqueous solution containing a vaccine antigen or immunogen capable of inducing an immune response in a host;
(2) a non-ionic hydrophilic surfactant having a high hydrophilic-lipophilic balance (HLB) value greater than 13 and less than 40, in particular $HLB \geq 13.5$, and preferably $HLB \geq 14$;
(3) a mineral oil;
(4) a non-ionic lipophilic surfactant; and
(5) a non-ionic hydrophilic surfactant having a low HLB value (HLB value between 9 and 13).

The emulsions made according to the present invention are based on a combination of at least 3 surfactants chosen among the members of three different groups of surfactants, and it is possible to use one or more surfactant pertaining to each group.

In a preferred embodiment, the concentration of non-ionic hydrophilic surfactant (5) in the emulsion (in the present specification this means the final emulsion comprising all ingredients unless otherwise indicated) is from 1% to 8%, in particular from 1.5% to 6%, preferably from 2% to 5%, more preferably from 2.5% to 4%, expressed as a percentage in weight by volume of emulsion (w/v).

This group of surfactants comprises non-ionic hydrophilic surfactants having a low HLB value (HLB value between 9 and 13). This group includes but is not limited to ethoxylated fatty acid monoester of sorbitan (in particular 5 ethoxyl groups) (e.g. ethoxylated sorbitan monooleate such as Tween 81®), ethoxylated fatty acid diesters of sorbitan, ethoxylated fatty acid triesters of sorbitan (in particular 20 ethoxyl groups) (e.g. ethoxylated sorbitan trioleate such as Tween 85®), ethoxylated sorbitan tristearate such as Tween 65®, ethoxylated fatty alcohols (in particular 5-10 ethoxyl groups) (e.g. Brij 76®, Brij 56®, Brij 96®), ethoxylated fatty acids (in particular 5-10 ethoxyl groups) (e.g. Simulsol 2599®, Myrj 45®), ethoxylated castor oil (in particular 25-35 ethoxyl groups) (e.g. Arlatone 650®, Arlatone G®), and combinations thereof.

Ethoxylated fatty acid diesters of sorbitan and ethoxylated fatty acid triesters of sorbitan are preferred, as well combinations of both species. The fatty acid is preferably selected from the group consisting of oleate, palmitate, stearate, isostearate, laurate and the combinations thereof. Preferred ethoxylated fatty acid triester of sorbitan comprise ethoxylated sorbitan trioleate such as Tween 85®), or ethoxylated sorbitan tristearate such as Tween 65®.

In a preferred embodiment, the concentration of non-ionic hydrophilic surfactant (2) is generally from 0.1% to 1.5%, in particular from 0.2% to 1.4%, preferably from 0.3% to 1.3%, more preferably from 0.4% to 1.2%, expressed as a percentage in weight by volume of emulsion (w./v).

This second group of surfactants comprises non-ionic hydrophilic surfactants having a high hydrophilic-lipophilic balance (HLB) value (HLB>13, in particular HLB≧13.5, and preferably HLB≧14). This group comprises ethoxylated fatty acid monoesters of sorbitan (in particular 20 ethoxyl groups) (e.g. ethoxylated sorbitan monolaurate such as Tween 20®, ethoxylated sorbitan monopalmitate such as Tween 40®, ethoxylated sorbitan monostearate (such as Tween 60®, ethoxylated sorbitan monooleate such as Tween 80®, ethoxylated fatty alcohols (in particular 15-30 ethoxyl groups) (e.g. Brij 78®, Brij 98®, Brij 721®), ethoxylated fatty acids (in particular 15-30 ethoxyl groups) (e.g. Myrj 49®, Myrj 51®, Myrj 52®, Myrj 53®), non-ionic block-copolymers (e.g. polyoxyethylene/polyoxypropylene copolymer (POE-POP), 1 such as Lutrol F127®, Lutrol F68®), and combinations thereof.

For the non-ionic block-copolymers, the percentages may be lower and be in particular from 0.1% to 0.5%, more particularly from 0.2% to 0.4% (weight by volume of emulsion (w/v)).

Preferred surfactants (2) comprise ethoxylated fatty acid monoesters of sorbitan, such as those described above.

In a preferred embodiment, the concentration of non-ionic lipophilic surfactant (4) is from 0.1% to 2.5%, in particular from 0.2% to 2%, preferably from 0.2% to 1.5%, more preferably from 0.2% to 1.2%, expressed as a percentage in weight by volume of emulsion (w/v).

This group of surfactants comprises fatty acid esters of sorbitan (e.g. sorbitan monolaurate, like Span 20®, sorbitan monopalmitate, such as Span 40®, sorbitan monostearate, such as Span 60®, sorbitan tristearate, such as Span 65®, sorbitan monooleate, like Span 80®, sorbitan trioleate, like Span 85®, sorbitan monoisostearate, such as Arlacel 987®, sorbitan isostearate, such as Crill 6®), fatty acid esters of mannide (e.g. Montanide 80®, mannide monooleate (such as Arlacel A®), mannide dioleate, mannide trioleate, mannide tetraoleate), ethoxylated fatty acid esters of mannide (2, 3 or 4 ethoxyl groups) (e.g. Montanide 888®, Montanide 103®, ethoxylated mannide monooleate, ethoxylated mannide dioleate, ethoxylated mannide trioleate, ethoxylated mannide tetraoleate), and combinations thereof.

The fatty acid is preferably selected from the group consisting of oleate, palmitate, stearate, isostearate, laurate and combinations thereof.

Preferred surfactants (4) comprise the fatty acid esters of sorbitan, in particular those described above, and combinations thereof.

The surfactants of the invention may have fatty acids from animal or vegetal origin. The change of one origin for the other (for example animal Tween 80® to vegetal Tween 80®) could be done simply with only minor adjustment in the formulation of the emulsion.

An emulsion according to the invention may have an overall concentration of surfactants, by weight per volume of emulsion, from 1.2% to 10%, in particular from 2% to 8%, preferably from 3% to 7%, more preferably from 4% to 6%.

Generally, the emulsion according to the invention may have a phase inversion temperature (PIT) which is ≧33° C., in particular ranges from 33° C. to 65° C., more particularly from 36° C. to 60° C., preferably from 37° C. to 55° C., and more preferably from 38° C. to 50° C.

The PIT is the temperature at which a water-in-oil emulsion changes to an oil-in-water emulsion or de-phases (breaks of the emulsion and separation of the 2 phases). The PIT value may be measured by various means, like for example by visual appearance (e.g. see example 2) or by conductivity. The emulsion is placed at a temperature below the PIT of the emulsion, for example of about 25° C. in a water-bath. The temperature is progressively increased. The change of the visual aspect of the emulsion is observed in comparison with a control emulsion, notably the fluidity, the viscosity, the separation in two phases, the change of the surface aspect due to the migration of the oily phase to the surface. The temperature, for which this change of visual aspect was observed, is the PIT value of the emulsion. Alternatively, the PIT is determined by the quick passage from a conductivity value of about 5-8 milliSiemens/centimetre (mS/cm) (oil-in-water emulsion) to a value of about 0 mS/cm (water-in-oil emulsion) measured by a probe placed into the emulsion, near its surface. The temperature, for which the transition was observed, is the PIT value of the emulsion. One of ordinary skill in the art will be able to determine combinations of surfactants and oil, including their respective concentrations, in order to produce emulsions according to the invention, and in particular emulsions having a PIT value within the ranges defined above without undue experimentation.

In a particular embodiment of the present invention, an emulsions as described herein does not contain any ionic surfactant or any compound known to have ionic surfactant properties, such as lecithin or saponin. Generally, emulsions according to the present invention may contain, by volume per volume of emulsion, from 3% to 55% of oil, in particular from 5% to 50% of oil, preferably from 10% to 40% of oil and, more preferably, from 20% to 40% of oil. By definition, ranges of values in the present specification include always the limit of the range, unless otherwise indicated.

The oil used may be a mineral oil including, but not limited to, paraffin oil such as isoparaffinic oil and/or naphtenic oil, squalane, pristane, polyisobutene oil, hydrogenated polyisobutene oil, polydecene oil, polyisoprene oil, polyisopropene oil and the like. One advantageous mineral oil useful in the present invention may include an oil comprising a linear or ramified carbon chain having a number of carbon atoms greater than 15, preferably from 15 to 32, and free of aromatic compounds. Such oils may, for example, be those marketed under the name "MARCOL 52®" or "MARCOL 82®" (produced by Esso, France) or "DRAKEOL 6VR®" (produced by Penreco, USA).

The oil may also be a mixture of oils comprising at least 2 oils selected among the oils described herein, and in any proportion. The mixture of oils may also comprise at least one oil selected among the oils described above and at least one vegetable oil, and this vegetable oil represents from about 0.1% to about 33% of the oily phase, preferably from about 10% to about 25% v/v. These vegetable oils are unsaturated oils rich in oleic acid that are biodegradable and preferably liquid at the storage temperature (about +4 degree C.) or at least make it possible to give emulsions that are liquid at this temperature. For example the vegetable oil may be groundnut oil, nut oil, sunflower oil, safflower oil, soya oil, onager oil and the like.

In a preferred embodiment, hydrophilic surfactants (2) and (5) preferably include surfactants having the same hydrophilic part of the molecules. For instance, use is made of ethoxylated fatty acid esters of sorbitan for each of hydrophilic surfactants (2) and (5). For example if Tween 85® is chosen as non-ionic hydrophilic surfactants having a low HLB value, the non-ionic hydrophilic surfactant having a high HLB value will advantageously have a hydrophilic part constituted with an ethoxyletad sorbitan, such as Tween 80®.

Generally, the present invention envisions using an aqueous solution comprising a suitable veterinary or pharmaceutically acceptable vehicle, excipient, or diluent including, but not limited to, sterile water, physiological saline, glucose, buffer and the like. The vehicle, excipient or diluent may also include polyols, glucids or pH buffering agents. The vehicle, excipient or diluent may, for example, also comprise amino acids, peptides, antioxidants, bactericide, bacteriostatic compounds. The aqueous solution is added to the oil and the surfactants in quantity to obtain 100% of the volume of the emulsion according to the invention.

The hydrophilic-lipophilic balance HLB) of an emulsion allows for the estimation of the hydrophilic or lipophilic force of a surfactant. The HLB of an amphiphilic molecule is generally calculated as follow:

$$HLB = \frac{(20 \times \text{weight of the hydrophilic part})}{(\text{weight of the amphiphilic molecule})}$$

The HLB may have a value ranging from 0 (for the most lipophilic molecule) to 20 (for the most hydrophilic molecule). According to the chemical composition of the surfactant (notably for example the addition of ethoxyl groups or of alkene oxides), this estimation may change and the domain of HLB value may increase (for example, the Lutrol F68® has a HLB of 29). With a mixture of surfactants, the HLB of the mixture is the addition of the HLB of each surfactant, balanced by its weight ratio:

$$HLB = \frac{(HLB\ surfactantX \times \text{weight}\ surfactantX) + (HLB\ surfactantY \times \text{weight}\ surfactantY)}{(\text{weight}\ surfactantX + \text{weight}\ surfactantY)}$$

In one embodiment of an emulsion made according to the present invention, the final HLB of the emulsion is from about 9 to about 12, preferably from about 9.5 to about 11.5 and more preferably from about 10 to about 11.5.

The present invention contemplates an emulsion comprising a paraffin oil (in particular at a concentration of from about 10% to a bout 40% and preferably from about 20% to about 40%, expressed as a volume per volume of emulsion (v/v)); a sorbitan fatty acid monoester (as non-ionic lipophilic surfactant), an ethoxylated fatty acid triester of sorbitan (as non-ionic hydrophilic surfactant having a low HLB value); and an ethoxylated fatty acid monoester of sorbitan (as non-ionic hydrophilic surfactant having a high HLB value). In particular the sorbitan fatty acid monoester is a sorbitan monooleate (in particular at the concentration from 0.2% to 1.5%, preferably from 0.2% to 1.2% expressed as a weight per volume of emulsion (w/v)), the ethoxylated fatty acid triester of sorbitan is an ethoxylated trioleate of sorbitan (in particular at the concentration from 2% to 5%, preferably from 2.5% to 4% w/v)) and the ethoxylated fatty acid monoester of sorbitan is an ethoxylated sorbitan monooleate (in particular at the concentration from 0.3% to 1.3%, preferably from 0.4% to 1.2% w/v). For example the emulsion comprises the paraffin oil at about 29.3% by volume per volume of emulsion, the sorbitan monooleate at 0.6% by weight per volume of emulsion, the ethoxylated trioleate of sorbitan at 3.4% by weight per volume of emulsion, and the ethoxylated sorbitan monooleate at 0.75% by weight per volume of emulsion.

In a second embodiment according to the present invention, the emulsion comprises a paraffin oil (in particular at a concentration from 10% to 40%, preferably from 20% to 40% v/v), a sorbitan fatty acid monoester (as non-ionic lipophilic surfactant), an ethoxylated fatty acid triester of sorbitan (as non-ionic hydrophilic surfactant having a low HLB value), and a non-ionic block-copolymer (as non-ionic hydrophilic surfactant having a high HLB value). In particular the sorbitan fatty acid monoester is a sorbitan monooleate (in particular at the concentration from 0.2% to 1.5%, preferably from 0.2% to 1.2% w/v), the ethoxylated fatty acid triester of sorbitan is an ethoxylated trioleate of sorbitan (in particular at the concentration from 2% to 5%, preferably from 2.5% to 4% w/v) and the non-ionic block-copolymer is a polyoxyethylene/polyoxypropylene polymer (POE-POP) (in particular at the concentration from 0.1% to 0.5%, preferably from 0.2% to 0.4% w/v). For example the emulsion comprises the paraffin oil at about 29.3% v/v, the sorbitan monooleate at 0.6% w/v, the ethoxylated trioleate of sorbitan at 3.4% w/v, and the ethoxylated sorbitan monooleate at 0.25% w/v.

In a particular embodiment, the invention contemplates an injectable oil-in-water (O/W) emulsion comprising:

(1) an aqueous solution containing an active ingredient such as a drug or an immunogen, preferably an immunogen;
(2) a mineral oil;
(3) a non-ionic lipophilic surfactant; and
(4) a non-ionic hydrophilic surfactant having a low HLB value which comprises of an ethoxylated fatty acid diester of sorbitan (which may have a HLB value between 11 and 13).

An emulsion according to this embodiment comprises ethoxylated fatty acid diesters of sorbitan that may contain up to 20 ethoxy groups. The fatty acids may be from animal or vegetable origin and may be selected from the group consisting of oleate, palmitate, stearate, isostearate, laurate and combinations thereof. In one embodiment the ethoxylated fatty acid is preferably oleate. The other ingredients, as well as the general properties of the emulsion such as the PIT, may have the same characteristics than those described above.

Preferably, surfactant (4) comprises ethoxylated fatty acid diesters of sorbitan, such as ethoxylated sorbitan dioleate, ethoxylated sorbitan distearate or ethoxylated sorbitan diisostearate, ethoxylated sorbitan dipalmitate, ethoxylated sorbitan dilaurate, and combinations thereof.

Optionally other compounds may be added as co-adjuvants to the emulsion, including, but not limited to, alum; CpG oligonucleotides (ODN), in particular ODN 2006, 2007, 2059, or 2135 (Pontarollo R. A. et al., *Vet. Immunol. Immunopath*, 2002, 84: 43-59; Wernette C. M. et al., *Vet. Immunol. Immunopath*, 2002, 84: 223-236; Mutwiri G. et al. *Vet. Immunol. Immunopath*, 2003, 91: 89-103); polyA-polyU ("Vaccine Design The Subunit and Adjuvant Approach", edited by Michael F. Powell and Mark J. Newman, *Pharmaceutical Biotechnology*, 6: 03); dimethyldioctadecylammonium bromide (DDA) ("Vaccine Design: The Subunit and Adjuvant Approach", edited by Michael F. Powell and Mark J. Newman, *Pharmaceutical Biotechnology*, volume 6: 157), N,N-dioctadecyl-N',N'-bis(2-hydroxyethyl)propanediamine (such as Avridine®) (Ibid, p. 148), carbomer, chitosan (see U.S. Pat. No. 5,980,912 for example).

The present invention also provides a method of making a vaccine composition or immunologic composition comprising at least one antigen or immunogen and an adjuvant or emulsion made according to the present invention. The immunogen may be incorporated during emulsion formation or, in an alternate embodiment, the immunogen may be added to the emulsion later as, for example, just before use.

The entire amount of the aqueous solution used may be present in the emulsion first produced. Or it may be that only a part of this aqueous solution is used to form the emulsion, and the remaining quantity of aqueous solution is added after incorporation of the immunogen. The immunogen or antigen may be in a lyophilized form or present in some other appropriate solid form and then mixed with the emulsion or, alternately, the antigen may be in solution, in particular in an aqueous solution, and this solution mixed with the emulsion.

Surfactants are preferably added to either the oil or the aqueous solution according to their solubility. For example, the non-ionic lipophilic surfactants are added to the oil according to the invention while non-ionic hydrophilic surfactants having a high HLB value are added to the aqueous solution.

The emulsification can be prepared according to conventional methods known to one of ordinary skill in the art. For example, in one embodiment of the present invention, the emulsion can be prepared at a temperature below the PIT of the emulsion, in particular at room temperature, e.g. at about 25° C. The aqueous phase and the oily phase are mixed together by a mechanical agitation, e.g. with a turbine equipped with a rotor-stator able to create a high shearing force. Preferably the agitation starts at a low rotation speed and slowly increases in relation to the progressive addition generally of the aqueous solution in the oil. Preferably the aqueous solution is progressively added to the oil. The ratio of oil/aqueous solution may be adapted to obtain a water-in oil (W/O) emulsion, for example, at a concentration of about 40% to about 55% of oil (v/v). When the agitation is stopped, the emulsion changes progressively to an O/W emulsion (phase inversion). After inversion and if needed, the emulsion is diluted by addition of an aqueous solution to obtain the desired concentration of oil into the final emulsion. The emulsion may be stored at about 5° C.

In another embodiment, the emulsion can be prepared at a temperature higher than the PIT of the emulsion. In a first step, the aqueous phase and the oily phase are mixed together at a temperature higher than the PIT of the emulsion. Preferably the aqueous solution is progressively added to the oil. The ratio of oil/aqueous solution may be adapted to obtain a water-in oil (W/O) emulsion, for example at a concentration of about 40% to about 55% of oil (v/v). The emulsification may be done by an agitation with low or no shearing force, e.g. with a static mixer or a marine helix or with a turbine at a very low rotation speed. The emulsion obtained is a water-in-oil (W/O) emulsion. In a second step, the emulsion is cooled progressively below the PIT. During this step, the emulsion changes to an O/W emulsion (phases inversion). After inversion and if needed, the emulsion is diluted by addition of an aqueous solution to obtain the desired concentration of oil into the final emulsion. The emulsion may be stored at about 5° C.

The size of the droplets in the emulsion may be from about 100 nm to about 500 nm. The emulsion may be used, for example, as an adjuvant to formulate a vaccine composition or a pharmaceutical composition. The emulsion may also be used as a solvent to dissolve a dried product, especially a lyophilised product containing, for example, attenuated microorganisms or live recombinant vectors.

In a particular embodiment, a pre-emulsion is produced with only a part of the aqueous solution. This pre-emulsion may be diluted by addition of a suspension of an active ingredient such as a drug or an immunogen, preferably an immunogen, to obtain the final composition. Alternatively, the pre-emulsion may be diluted with an aqueous solution and used to dissolve a dried product such as a lyophilised product.

The immunogen or antigen suitable for use in the present invention may be selected from the group consisting of inactivated pathogens, attenuated pathogens, immunogenic sub-units (e.g. proteins, polypeptides, peptides, epitopes, haptens), or recombinant expression vectors, including plasmids having immunogenic inserts. In one embodiment of the present invention, the immunogen is an inactivated or killed microorganism. In another embodiment of the invention, the vaccine composition comprises an immunogen selected from the group of avian pathogens including, but not limited to, *Salmonella typhimurium, Salmonella enteritidis*, Infectious Bronchitis virus (IBV), Newcastle Disease virus (NDV), egg drop syndrome virus (EDS), or Infectious Bursal Disease virus (IBDV), avian influenza virus, and the like, and combinations thereof.

Alternately, the vaccine composition comprises an immunogen selected from a feline pathogen such as, but not limited to, feline herpesvirus (FHV), feline calicivirus (FCV), feline leukemia virus (FeLV), feline immunodeficiency virus (FIV), rabies virus, and the like, and combinations thereof.

In yet another embodiment, a vaccine composition of the present invention comprises an immunogen selected from a canine pathogen including, but not limited to, rabies virus, canine herpesvirus (CHV), canine parvovirus (CPV), canine coronavirus, *Leptospira canicola, Leptospira icterohaemorragiae, Leptospira grippotyphosa, Borrelia burgdorferi, Bordetella bronchiseptica* and the like, and combinations thereof.

In yet another embodiment of the invention the composition comprises an immunogen selected from an equine pathogen, such as equine herpesvirus (type 1 or type 4), equine influenza virus, tetanus, west nile virus, and the like or combinations thereof.

In yet another embodiment of the invention, the composition comprises an immunogen selected from an bovine pathogen, such as rabies virus, bovine rotavirus, bovine parainfluenza virus type 3 (bPIV-3), bovine coronavirus, bovine viral diarrhea virus (BVDV), foot and mouth disease virus (FMDV), bovine respiratory syncytial virus (BRSV), Infectious Bovine Rhinotracheitis virus (IBR), *Escherichia coli, Pasteurella multocida, Pasteurella haemolytica* and the like and combinations thereof.

In still another embodiment of the present invention, the composition comprises an immunogen selected from an porcine pathogen such as, but not limited to, swine influenza virus (SIV), porcine circovirus type 2 (PCV-2), porcine reproductive respiratory syndrome virus (PRRS), pseudorabies virus (PRV), porcine parvovirus (PPV), FMDV, *Mycoplasma hyopneumoniae, Erysipelothrix rhusiopathiae, Pasteurella multocida, Bordetella bronchiseptica, Escherichia coli* and the like, and combinations thereof.

A preferred embodiment of the invention provides for vaccine compositions comprising at least one immunogen and an emulsion in a pharmaceutically acceptable vehicle. Immunogens comprising viruses, bacteria, fungi and the like may be produced by in vitro culture methods using appropriate culture medium or host cells lines and conventional methods well known to those of ordinary skill in the art. For example, PRRS may be cultured in an appropriate cell line, such as MA-104 cell line (see U.S. Pat. Nos. 5,587,164; 5,866,401; 5,840,563; 6,251,404 among others). In a similar manner, PCV-2 may be cultured using PK-15 cells line (see U.S. Pat. No. 6,391,314); SIV may be cultured on eggs (U.S. Pat. No. 6,048,537); and *Mycoplasma hyopneumoniae* may be cultured in a appropriate culture medium (U.S. Pat. No. 5,968,525; U.S. Pat. No. 5,338,543; Ross R. F. et al., *Am. J. Vet. Res.*, 1984, 45: 1899-1905).

In order to obtain an inactivated immunologic, or vaccine composition, the pathogen is preferably inactivated after harvesting and, optionally, subjected to clarification by means of a chemical treatment using, for example, formalin or formaldehyde, beta-propiolactone, ethyleneimine, binary ethyleneimine (BEI), thimerosal, and the like, and/or a physical treatment (e.g. a heat treatment or sonication). Methods for inactivation are well known to those of skill in the art. For example, the PRRS virus may be inactivated by beta-propiolactone treatment (Plana-Duran et al., *Vet. Microbiol.*, 1997, 55: 361-370) or by BEI treatment (U.S. Pat. No. 5,587,164); inactivation of PCV-2 virus may be accomplished using ethyleneimine treatment or by beta-propiolactone treatment (U.S. Pat. No. 6,391,314); swine influenza virus may be inactivated using a detergent like Triton, or with formaldehyde treatment (U.S. Pat. No. 6,048, 537); *Mycoplasma hyopneumoniae* bacterium may be inactivated by formaldehyde treatment (Ross R. F. supra), by ethylenimine or BEI treatment (see WO 91/18627), or by thimerosal treatment (U.S. Pat. Nos. 5,968,525 and 5,338, 543).

The inactivated pathogen can be concentrated by conventional concentration techniques, in particular by ultrafiltration, and/or purified by conventional purification means, in particular using chromatography techniques including, but not limited to, gel-filtration, ultracentrifugation on a sucrose gradient, or selective precipitations, in particular in the presence of polyethylene glycol (PEG).

Immunogens useful in vaccine compositions according to the present invention also include expression vectors. Such vectors include, but are not limited to, in vivo recombinant expression vectors such as a polynucleotide vector or a plasmid (EP-A2-1001025; Chaudhuri P, *Res. Vet. Sci.* 2001, 70: 255-6), virus vectors such as, but not limited to, adenovirus vectors, poxvirus vectors such as fowlpox (U.S. Pat. Nos. 5,174,993; 5,505,941; and 5,766,599) or canarypox vectors (U.S. Pat. No. 5,756,103) or bacterial vectors (*Escherichia coli* or *Salmonella* sp.)/.

The present invention also encompasses the formulation of multivalent immunological compositions or combination vaccine compositions. For example, antigens useful in a combination bovine bacterin made according to the present invention of the present invention include, but are not limited to, *Mycoplasma bovis*, *Pasteurella* sp., particularly *P. multocida* and *P. haemolytica*, *Haemophilus* sp., particularly *H. somnus*, *Clostridium* sp., *Salmonella*, *Corynebacterium*, *Streptococcus*, *Staphylococcus*, *Moraxella*, *E. coli* and the like.

The present invention further provides for methods for inducing an immune response in a host, e.g., an animal, comprising administering to the host an immunological composition or a vaccine composition according to the invention. The immune responses elicited in this manner are notably antibody and/or cellular immune responses, and in particular, a gamma-interferon response.

In particular, the present invention provides for methods to immunize against, or to prevent or to reduce the symptoms caused by, infection of an animal with a pathogenic organism (for example, infection by a virus, bacteria, fungus, or protozoan parasite). The method of the present invention is useful in vertebrate animals including, but not limited to, humans, canines (e.g., dogs), felines (e.g., cats); equines (e.g., horses), bovines (e.g., cattle) and porcine animals (e.g., pigs), as well as in avians including, but not limited to, chickens, turkeys, ducks, geese, a quail, a pheasant, parrots, finches, hawks, crows and ratites (ostrich, emu, cassowary, and the like).

In a particular aspect of the invention, these methods consist of the vaccination of pregnant females before parturition by administering a vaccine composition made according to the invention. These methods further include the induction of protective antibodies elicited by the vaccination protocol and the transfer of these protective antibodies from vaccinated pregnant females to their offspring. The transfer of such maternal antibodies subsequently protects the offspring from disease.

The dosage of the vaccine composition made according to the present invention will depend on the species, breed, age, size, vaccination history, and health status of the animal to be vaccinated. Other factors like antigen concentration, additional vaccine components, and route of administration (i.e., subcutaneous, intradermal, oral, intramuscular or intravenous administration) will also impact the effective dosage. The dosage of vaccine to administer is easily determinable based on the antigen concentration of the vaccine, the route of administration, and the age and condition of the animal to be vaccinated. Each batch of antigen may be individually calibrated. Alternatively, methodical immunogenicity trials of different dosages, as well as $LD_{50}$ studies and other screening procedures can be used to determine effective dosage for a vaccine composition in accordance with the present invention without undue experimentation. From the examples presented below, it will be readily apparent what approximate dosage and what approximate volume would be appropriate for using the vaccine composition described herein. The critical factor is that the dosage provides at least a partial protective effect against natural infection, as evidenced by a reduction in the mortality and morbidity associated with natural infection. The appropriate volume is likewise easily ascertained by one of ordinary skill in the art. For example, in avian species the volume of a dose may be from about 0.1 ml to about 0.5 ml and, advantageously, from about 0.3 ml to about 0.5 ml. For feline, canine and equine species, the volume of a dose may be from about 0.2 ml to about 3.0 ml, advantageously from about 0.3 ml to about 2.0 ml, and more advantageously, from about 0.5 ml to about 1.0 ml. For bovine and porcine species, the volume of dose may be from about 0.2 ml to about 5.0 ml, advantageously from about 0.3 ml to about 3.0 ml, and more advantageously from 0.5 ml to about 2.0 ml.

Repeated vaccinations may be preferable at periodic time intervals to enhance the immune response initially or when a long period of time has elapsed since the last dose. In one embodiment of the present invention, the vaccine composition is administered as a parenteral injection (i.e., subcutaneously, intradermally, or intramuscularly). The composition may be administered as one dose or, in alternate embodiments, administered in repeated doses of from about two to about five doses given at intervals of about two to about six weeks, preferably from about two to about five weeks. However, one of skill in the art will recognize that the number of doses and the time interval between vaccinations depends on a number of factors including, but not limited to, the age of the animal vaccinated; the condition of the animal; the route of immunization; amount of antigen available per dose; and the like. For initial vaccination, the period will generally be longer than a week and preferably will be between about two to about five weeks. For previously vaccinated animals, a booster vaccination, before or during pregnancy, at about an annual interval may be performed.

The present invention also contemplates administering a vaccine composition using a needlefree injector such as Pigjet®, Avijet®, Dermojet® or Biojector® (Bioject, Oregon, USA). An person of ordinary skill in the art is able to adjust the specifications of the injector as required with regard to factors such as the species of the animal to be vaccinated; the age and weight of the animal, and the like without undue experimentation.

In one embodiment of the present invention, the method comprises a single administration of a vaccine composition formulated with an emulsion according to the invention. For example, in one embodiment, the vaccine composition is an inactivated *Mycoplasma hyopneumoniae* vaccine, while an alternate embodiment provides for a vaccine comprising an inactivates PCV2 virus composition. Other immunological compositions or vaccines are suitable for use in a single dose regimen including, but not limited to, inactivated PRRS and SIV. In particular, for the *Mycoplasma hyopneumoniae* vaccine composition, the single dose may be administered between the birth and the slaughtering of a pig, in particular between about 3 to about 56 days of age, preferably between about 10 to about 35 days of age, more preferably between about 15 and about 30 days of age. The vaccine may be administered also in presence of pre-existing antibodies.

The invention further relates to methods to treat a host, e.g., an animal, comprising administering to the host a pharmaceutical composition made according to the invention and comprising at least one immunogen selected from the group consisting of proteins or peptides, antibodies, allergens, CpG ODN, growth factors, cytokines, or antibiotics, and in particular CpG ODN or cytokines. These pharmaceutical compositions can be used to improve growth performances in an animal such as a chicken, a pig, or a cow.

The present invention further relates to a kit comprising a first vial containing an ingredient such as an immunogen or pharmaceutical composition and, in a second vial, an emulsion made according to the present invention. The immunogen may be in a lyophilized form, a dried form or in aqueous solution as described herein.

The invention will now be further described by way of the following non-limiting examples.

EXAMPLE 1

Emulsion Manufacturing Method

The emulsion is produced in two steps as described as follows:

First Step: A high shear rotor-stator Silverson emulsifier (L4RT type with a disintegrating head with a diameter of 10 mm) was used to produce the formulations. To produce an emulsion, one volume of oily phase was emulsified at 25° C. with one volume of aqueous phase #1. The aqueous phase was added to the oily phase under agitation, 5000 rpm (rotation per minute) for 1 minute. The rotation speed was progressively increased with the augmentation of the volume to 8300 rpm during 1 minute. During this step the emulsion was a water-in-oil emulsion. For the TS6 emulsion, phase composition was as follows:

Oily Phase (120 ml):

| | |
|---|---|
| Sorbitan monooleate (Span 80 ®): | 1.8% w/v, |
| Sorbitan trioleate (20 OE) (Tween 85 ®): | 10.2% w/v, |
| Paraffin oil (Marcol 82 ®): | 88% v/v, |

Aqueous Phase #1 (120 ml):

| | |
|---|---|
| 20% (w/v) solution of sorbitan monooleate (20 OE) (Tween 80 ®): | 11.25% w/v |
| Phosphate disodic and monopotassic 0.02 M isotonic buffer (pH 7.8): | 85.75% v/v |
| Sodium mercurothiolate (Thiomersal ®) 1% in water: | 1.5% v/v |

Sorbitan monooleate (Span 80®) and sorbitan trioleate (20 OE) (Tween 85®)) were introduced in the oily phase. The sorbitan monooleate (20 OE) (Tween 80®) was not miscible in the paraffin oil. A 20% (w/v) solution of Tween 80® was prepared in the same buffer as the vaccine, for example, in phosphate disodic and monopotassic 0.02M isotonic buffer (pH 7.8). Sodium mercurothiolate acts as a preservative and is not essential for the emulsion.

When the agitation stopped, the emulsion changed to an oil-in-water emulsion. The emulsion was placed in a cold chamber at 5° C. for at least 4 hours. At this stage, the emulsion was a pre-emulsion containing 50% of oily phase.

Second Step: The aqueous phase #2 was prepared with 120 ml of phosphate disodic and monopotassic 0.02M isotonic buffer pH 7.8 with immunogens (inactivated *Mycoplasma hyopneumoniae* immunogen, or PCV-2 immunogen, as described infra). The pre-emulsion as prepared in the first step was cooled to about 5° C., diluted by adding half the volume of the aqueous phase #2 at the same temperature, and mixed by the rotation of a magnetic bar for 1 minute. Final surfactant concentration in the TS6 emulsion was 4.75% (w/v).

As prepared herein, the TS6 vaccines are stable for at least one year at 5° C.

Using the same preparation method, other emulsions can be obtained as described below:

TS7 Emulsion

The TS7 emulsion is an O/W emulsion containing 33% of an oily phase. The oily phase (120 ml) contains Marcol 82®) 88% v/v, Span 80®) 1.8% w/v and Tween 85® 10.2% w/v. The aqueous phase #1 (120 ml) contains phosphate disodic and monopotassic 0.02M isotonic buffer (pH 7.8) 97.75% v/v, Thiomersal® 1% in water 1.5% v/v and Lutrol F127® 0.75% w/v. The aqueous phase #2 (120 ml) is constituted with the phosphate disodic and monopotassic 0.02M isotonic buffer (pH 7.8), optionally containing immunogens. Final surfactant concentration in the TS7 emulsion is 4.25% w/v.

TS8 Emulsion

The TS8 emulsion is an O/W emulsion containing 50% of an oily phase. The oily phase (160 ml) contains Marcol 82® 92% v/v, Span 85®) 1.8% w/v and Brij 96® 6.2% w/v. The aqueous phase #1 (160 ml) contains phosphate disodic and monopotassic 0.02M isotonic buffer (pH 7.8) 98.5% v/v, Thiomersal®) 1% in water 1.0% v/v and Lutrol F127® 0.5% w/v, optionally containing immunogens. Final surfactant concentration in the TS8 emulsion is 4.25% w/v.

TS9 Emulsion

The TS9 emulsion is an O/W emulsion containing 10% of an oily phase. The oily phase (120 ml) contains Marcol 82® 60% v/v, Span 40® 17.2% w/v and Arlatone 650® 22.8% w/v. The aqueous phase #1 (120 ml) contains phosphate disodic and monopotassic 0.02M isotonic buffer (pH 7.8) 97.5% v/v and Tween 20® 2.5% w/v. The aqueous phase #2 was prepared with 400 ml of phosphate disodic and monopotassic 0.02M isotonic buffer pH 7.8, optionally containing immunogens. 100 ml of the pre-emulsion was diluted with the 400 ml of the aqueous phase #2 to obtain the TS9 emulsion. Final surfactant concentration in the TS9 emulsion is 4.25% w/v.

EXAMPLE 2

Determination of the Phase Inversion Temperature (PIT) of an Emulsion 10 ml of the TS6 emulsion was placed into a glass tube in a water-bath at a temperature of about 25° C. The TS6 emulsion was a white homogeneous emulsion. The temperature in the water bath was progressively increased. Changes in the emulsion were visually observed (the emulsion became two separated phases due to the migration of the yellow-brown oily phase to the surface). This change is characteristic of the break down of the emulsion. The temperature at which this change is observed is the PIT value of the emulsion. For the TS6 emulsion, the PIT was 40-45° C., while the PIT for the TS7 emulsion was 44-49° C.

EXAMPLE 3

*Mycoplasma hyopneumoniae* Vaccine Composition and Heterologous Challenge

Materials and Methods: the vaccine composition was formulated containing the TS6 emulsion, prepared as described in Example 1, and inactivated *Mycoplasma hyopneumoniae*, BQ14 strain (Kobisch M. et al., *Ann. Inst. Pasteur Immunol.*, 1987, 138:693-705) at a concentration of 8.7 log10 CCU (color changing unit) per ml of vaccine. Twenty-two (22) piglets, three weeks old and having maternal antibodies (born from sows seropositive for *Mycoplasma hyopneumoniae*) were randomly allocated into two groups. One group of ten (10) piglets was vaccinated on day 0 with 2 ml of the vaccine composition by intramuscular injection, while the control group of twelve (12) piglets was not vaccinated.

At selected intervals during the experiment (days 0, 27, 42, and 56), nasal swabs were taken from piglets in both groups and anti-BQ14 secretory antibodies determined by ELISA. At day 27, piglets were bled and peripheral blood mononuclear cells (PBMN) obtained to determine IFNγ levels in the peripheral blood. At day 28, all piglets were challenged intranasally with a solution containing approximately 6.6 $\log_{10}$ CCU/ml of *Mycoplasma hyopneumoniae* Mp88c strain (strain isolated from a sick pig in Denmark and cultivated as described by Kobisch and Friis in *Rev. Sci. Tech. Off. Int. Epiz.* 1996, 15: 1569-1605) with approximately 5 mL being applied to each nostril. The challenge was repeated 24 hours later. Pigs were sacrificed and lungs collected at necropsy. Lung scores were determined by estimating the surface area (expressed in percentage of the whole lobe surface) of the lesion for each of the seven pulmonary lobes. Scores were assigned as follows:

| Surface of the lung lesion per lobe | Score |
|---|---|
| 0% | 0 |
| 1-25% | 1 |
| 26-50% | 2 |
| 51-75% | 3 |
| >75% | 4 |

A total score was calculated by adding the scores obtained for the individual lobes of each lung, resulting in a maximum score per animal of 28.

Results: Pigs vaccinated with the TS6 vaccine formulation exhibited a strong cellular response, and one that was significantly higher than the control group, as demonstrated by the number of spots secreting IFNγ from $5 \times 10^5$ P peripheral blood mononuclear cells (PBMN). Pigs from the vaccinated group averaged 139 spots (standard deviation 25) as compared to 11 (standard deviation of 5) in the unvaccinated controls.

| Groups | Number of spots for $5 \times 10^5$ PBMNCs |
|---|---|
| TS6 vaccine composition | 139 (25) |
| Untreated Controls | 11 (5) |

Levels of anti-BQ14 secretory antibodies in vaccinates and controls are summarized in the following table, with results showing that vaccinated pigs had significantly higher levels of secretory antibodies two to three weeks after challenge, as compared to untreated controls:

| | Anti-BQ14 secretory-antibodies (optical density (OD) values) | | | |
|---|---|---|---|---|
| Groups | D0 (before vaccination) | D27 (before challenge test) | D42 (14 days after challenge test) | D56 (28 days after challenge test) |
| TS6 | 0.026 ± 0.001 | 0.033 ± 0.002 | 0.201 ± 0.089 | 0.264 ± 0.043 |
| Controls | 0.030 ± 0.001 | 0.031 ± 0.001 | 0.107 ± 0.028 | 0.075 ± 0.011 |

Referring now to FIG. 1, animals vaccinated with the TS6 vaccine composition exhibit an average lung score of 2.1±1.9 (mean±standard deviation) as compared to the untreated controls with an average lung score of 7.8+/−4.1. These results show a significant reduction in lung lesions for the pigs vaccinated with the vaccine composition as compared to the unvaccinated controls.

EXAMPLE 4

Duration of Protection against a *Mycoplasma Hyopneumoniae* Heterologous Challenge Materials and Methods: Thirty-eight (38) piglets, three-weeks old with maternal antibodies (born from sows that were seropositive for *Mycoplasma hyopneumoniae*) were randomly allocated into three groups as follows:

Group 1 (12 piglets) were vaccinated via an intramuscular route on day 0 with 2 ml of the vaccine composition as described in Example 3.

Group 2 (12 piglets) were vaccinated on day 0 by intramuscular injection with 2 ml of a commercial *Mycoplasma hyopneumoniae* inactivated vaccine.

Group 3 (14 piglets) served as unvaccinated controls.

All piglets were intranasally challenged 20 weeks after vaccination with about 5 ml/per nostril of a *Mycoplasma hyopneumoniae* Mp88c challenge strain (6.6 log10 CCU/ml) as described above. The challenge was repeated 24 hours later. Blood was collected from all groups and peripheral blood mononuclear cells (PBMN) obtained to determine IFNγ levels as described above. Anti-BQ14 IgA and IgG1 serum antibodies were determined on Day 138 for each group. Following necropsy, lung scores (mean±standard deviation) were calculated as described in Example 3 above.

Figure 2:
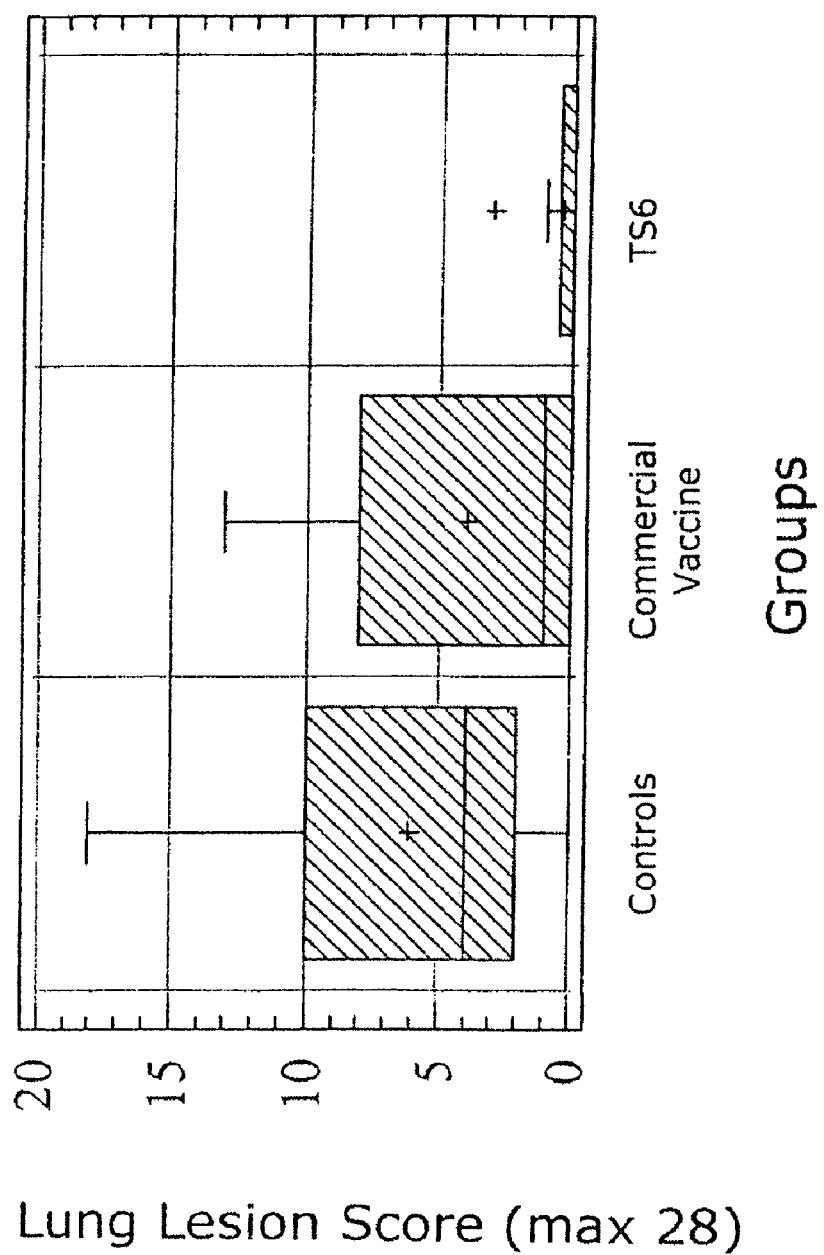
FIG. 2 illustrates lung lesion scores of piglets challenged 20 weeks after vaccination according to example 4. The mean value is shown by a cross, the lower quartile and the upper quartile by a box, the statistical median by a horizontal line in the box, the minimum to the maximum value by a vertical line.

Results: Referring now to FIG. 2, piglets from Group 1 vaccinated with the TS6 vaccine composition demonstrated an average lung score of 0.4±0.9, a statistically significant reduction from the lung score of piglets vaccinated with the commercial vaccine (4.0±5.1) or the unvaccinated controls (6.1±5.8).

The average results (+the standard deviation) of anti-BQ14 IgA and IgG1 circulating antibodies in serum collected from each group on Day 138 are summarized as follows:

| Groups | Anti-BQ14 IgG (titer) | Anti-BQ14 IgA |
|---|---|---|
| TS6 vaccine | 4.38 ± 0.14 | 0.56 ± 0.06 |
| Commercial vaccine | 3.09 ± 0.11 | 0.09 ± 0.01 |
| Controls | 2.73 ± 0.08 | 0.09 ± 0.01 |

The following table summarizes the average results (±the standard deviation) in number of spots for $5 \times 10^5$ peripheral blood mononuclear cells (PBMN) secreting gamma-interferon (IFNγ) in the peripheral blood:

| Groups | D28 | D138 | Day152 |
|---|---|---|---|
| TS6 vaccine | 81 ± 20 | 9 ± 2 | 28 ± 7 |
| Commercial vaccine | 5 ± 2 | 3 ± 1 | 6 ± 1 |
| Controls | 6 ± 3 | 2 ± 2 | 11 ± 8* |

*if a piglet expressing an abnormally high number of spots (109) is excluded, the mean of the control group is 4 ± 1.

As expected when using an inactivated vaccine, the frequency of anti-BQ14 IFNγ secreting T-cells detectable at day 138 post-vaccination was much lower than at day 28. Interestingly, most of the pigs vaccinated with TS6 were still positive at day 138 suggesting that the cellular response was maintained in this group. The frequency of anti-BQ14 IFNγ secreting T-cells circulating at day 152 (13 days post challenge) was very different between the three groups. The group vaccinated with TS6 developed a very high cellular response as opposed to the other groups. This result suggests that the challenge efficiently recalls the immune memory induced by the TS6 vaccine.

EXAMPLE 5

Serology Results after Administration of One Dose of a PCV-2 Vaccine Adjuvanted with the TS6 Emulsion Materials and Methods: Ten specific pathogen-free (SPF) piglets, 2-3 months old, were randomly allocated into 2 groups. One group of 5 piglets was vaccinated via an intramuscular route (on day 0) with 2 ml of a vaccine containing inactivated PCV-2 (imp1010 strain) at 6.8 log10 $CCID_{50}$ per dose (vaccinated group). The control group of 5 piglets was not vaccinated. Blood samples were taken at D0, D7, D14, D21 and D28 post vaccination for titration of the PCV-2 ORF2 antibodies by ELISA.

Results: As demonstrated in the following table, all the vaccinates showed a significant anti-PCV-2 ORF2 antibody response from 7 to 40 days after vaccination:

| Groups | ELISA (log10) | D0 | D7 | D14 | D21 | D28 |
|---|---|---|---|---|---|---|
| Vaccinated | Mean | 1.00 | 2.53 | 3.50 | 3.45 | 3.88 |
|  | Std deviation | 0.00 | 0.89 | 0.79 | 0.84 | 0.37 |
| Controls | Mean | 1.00 | 1.00 | 1.00 | 1.00 | 1.27 |
|  | Std deviation | 0.00 | 0.00 | 0.00 | 0.00 | 1.24 |

EXAMPLE 6

Protection against Challenge Elicited by a PCV-2 Vaccine Adjuvanted with the TS6 Emulsion Materials and Methods: sixteen (16) SPF piglets, 4-5 days old, were randomly allocated into 2 groups as follows: one group of 8 piglets was vaccinated twice by intramuscular injection on days 0 and 21 with 2 ml of the vaccine containing inactivated PCV-2 (imp1010 strain) at 7.55 log10 $CCID_{50}$ per dose (vaccinated group), while the control group of 8 piglets was not vaccinated. All the piglets were intranasally challenged on day 35 with PCV-2 Imp1011-48285 strain (deposited at the ECACC, under the accession number V98011608) containing about 5.5 log10 $CCID_{50}$ per ml with approximately 5 mL being applied to each nostril. Both ELISA and seroneutralization (SN) studies were performed and clinical scores determined for each piglet as follows:

|  | Score | | |
|---|---|---|---|
|  | 0 | 1 | 2 |
| Prostration | No | Moderate | High |
| Dyspnea | No | Moderate | High |
| Anemia (color of the piglet skin) | Pink | White | Yellow |
| Coughing | No | Yes |  |
| Anorexia | No | Yes |  |
| Vomiting | No | Yes |  |
| Rectal temperature | t < 40° C. | 39.9° C. < t < 41° C. | t > 40.9° C. |
| Weight gain during the week n is superior of the weight gain during the week n − 1 | Yes | No but > 100 g/day | No but < 101 g/day |
| Death | No | Yes* |  |

*In case of death, the score used is the value corresponding to the day before death.

Following necropsy, a lesion score was calculated as follows:

|                              | Score       |                                            |                                            |                                                               |
| ---------------------------- | ----------- | ------------------------------------------ | ------------------------------------------ | ------------------------------------------------------------- |
|                              | 0           | 1                                          | 2                                          | 3                                                             |
| Corpulence                   | Normal      | Lean                                       | Very lean                                  | Rachitic                                                      |
| Carcass aspect               | Normal      | White                                      | Yellow                                     |                                                               |
| Mucosa                       | Normal      | White                                      | Yellow                                     |                                                               |
| Subcutaneous connective tissue | Normal    | Bright                                     | Yellow                                     |                                                               |
| Superficial lymphatic ganglions | Normal   | 1 fat and/or white and/or congestive       | >1 fat and/or white and/or congestive      | >1 very fat and/or white and/or congestive                    |
| Thoracic discharge           | No          | Bright thoracic cavity                     | Visible presence                           |                                                               |
| Hearth                       | No lesion   | Lesion                                     |                                            |                                                               |
| Lung                         | No lesion   | Lesion                                     |                                            |                                                               |
| Pleura                       | No lesion   | Small lesions                              | Large lesions                              |                                                               |
| Mediastinal lymphatic ganglions | Normal   | 1 fat and/or white and/or congestive       | >1 fat and/or white and/or congestive      | >1 very fat and/or white and/or congestive                    |
| Abdominal cavity             | Normal      | Bright                                     | Visible ascites liquide                    |                                                               |
| Peritoneum                   | No lesion   | Lesion                                     |                                            |                                                               |
| Stomach                      | No lesion   | Lesion                                     | Ulcer                                      |                                                               |
| Small intestine              | No lesion   | Lesion                                     |                                            |                                                               |
| Intestine                    | No lesion   | Lesion                                     |                                            |                                                               |
| Mesenteritic lymphatic ganglions | Normal  | 1 fat and/or white and/or congestive       | >1 fat and/or white and/or congestive      | >1 very fat and/or white and/or congestive                    |
| Peyers plaques               | Not visible | Visible only in one intestinal segment     | Visible in several intestinal segments     | Visible in several intestinal segments and very important     |
| Liver                        | No lesion   | Lesion                                     |                                            |                                                               |
| Kidneys                      | No lesion   | Lesion                                     |                                            |                                                               |
| Bladder                      | No lesion   | Lesion                                     |                                            |                                                               |

Figure 3:
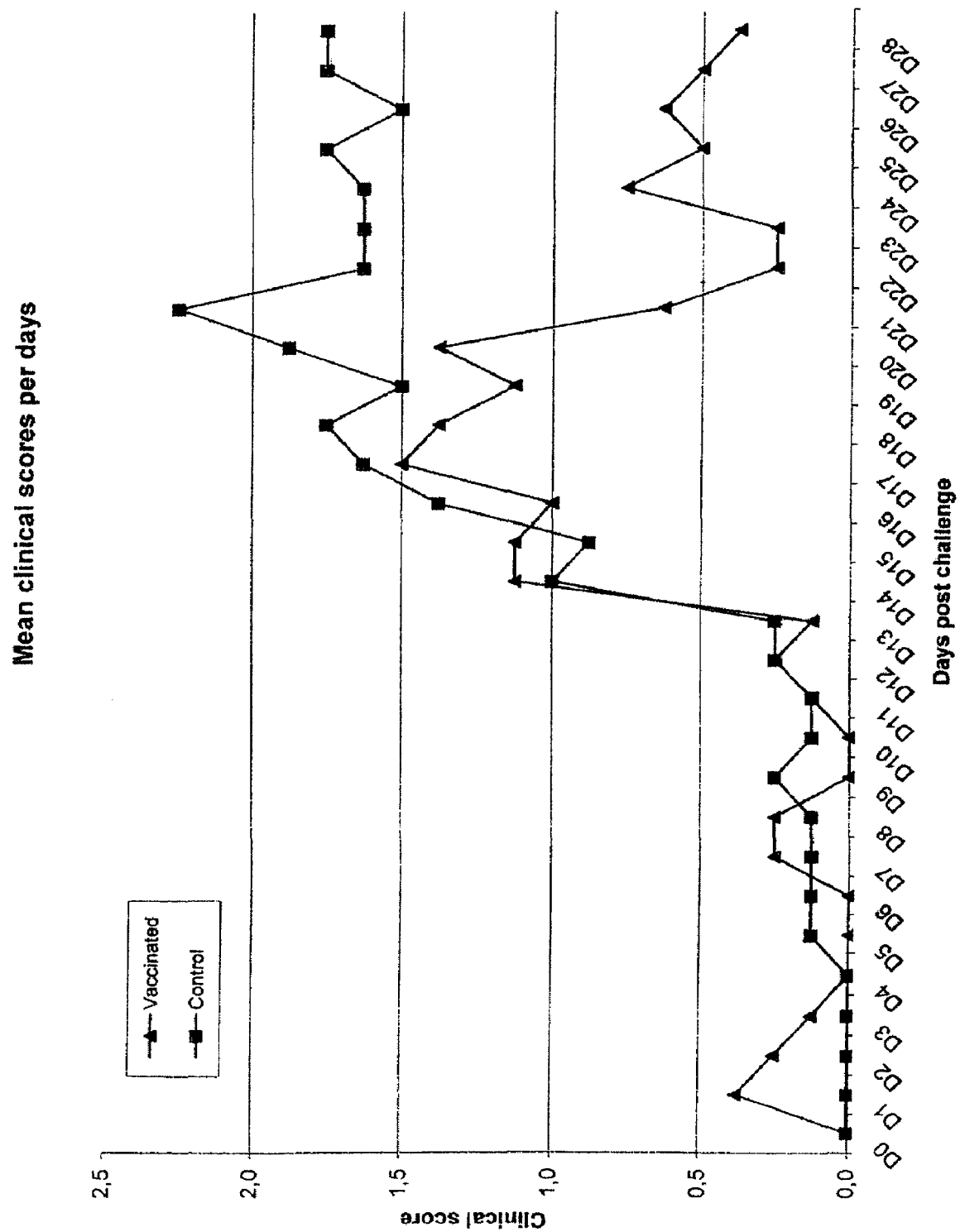
FIG. 3 provides a graph depicting the progression of clinical disease as exemplified by clinical score following challenge according to example 6.

Results: Results of serology as performed by ELISA and serum neutralizing antibody titers at days 30 and 63 show vaccinated piglets with higher levels than those seen in the untreated controls. The table below summarizes PCV-2 virus isolation results from fecal swabs and ganglionic tissue as well as shows average clinical and lesion scores from vaccinates and control groups. Results show higher levels of both circulating antibodies and SN titers in vaccinates as compared to controls. Clinical scores and lung lesions are significantly reduced in the vaccinated piglets as well. The evolution of the clinical score after challenge is shown in FIG. 3.

| Groups                                  | vaccinates    | controls      |
| --------------------------------------- | ------------- | ------------- |
| Serology ELISA at D30 (log10)           | 4.1 +/− 0.70  | 2.8 +/− 0.50  |
| Serology ELISA at D63 (log10)           | 5.2 +/− 0.28  | 3.4 +/− 0.67  |
| Serology SN at D30 (log10)              | 3.4 +/− 0.25  | 1.6 +/− 0.23  |
| Serology SN at D63 (log10)              | 3.7 +/− 0.31  | 2.2 +/− 0.53  |
| PCV-2 in feces (% of positives)         | 40            | 61            |
| PCV-2 in mediastinal ganglions (% of positives) | 25    | 100           |
| Clinical score                          | 14            | 31            |
| Lesion score                            | 9.8           | 18.8          |

EXAMPLE 7

Field Efficacy Results Following One Dose Vaccination with a TS6-Adjuvanted Inactivated PCV-2 Vaccine Vaccine composition: The TS6 adjuvant was prepared as described in Example 1. The PCV-2 virus was grown on PK/15 cells and viral multiplication carried out as described in U.S. Pat. No. 6,517,843 (Ellis et al.; the contents of which is hereby incorporated herein in its entirety). Briefly, at the end of viral culture, the infected cells are harvested, lysed and the viral harvest inactivated with conventional methods. For example, inactivation may be accomplished with 0.1% ethyleneimine for 18 hours at +37 degrees C.; with 0.5% beta-propiolactone for 24 hours at +28 degrees C.; or with 0.2% and 0.1% beta-propiolactone for 24 hours at +4 degrees C. If the virus titer before inactivation was inadequate, the viral suspension was concentrated by ultrafiltration using a membrane with a 150-300 kDa cut-off. The inactivated viral suspension was stored at +5 degrees C. before formulating the vaccine. The antigen content of the vaccine was set at 2.1 log 10 antigen Units per dose. Based on this content, the activity of the vaccine determined through the quantification of the active ingredient in the final product by an ELISA method was arbitrarily set at a minimum of 100 ELISA Units per dose.

Vaccination protocol: To test the efficacy of the vaccine composition under field conditions, a farm was chosen which typically exhibits endemic outbreaks of postweaning multisytemic wasting syndrome (PMWS) caused by PCV-2 infection in piglets. Sows were divided into two groups with vaccinates receiving one intramuscular injection (2 ml dose) of the TS6 adjuvanted PCV-2 inactivated vaccine two to three weeks before farrowing. The second group was not vaccinated and served as a control. The sows were allowed to farrow and piglets from vaccinated sows (n=889) and control sows (n=713) were monitored for mortality up to age of slaughter.

Figure 4:
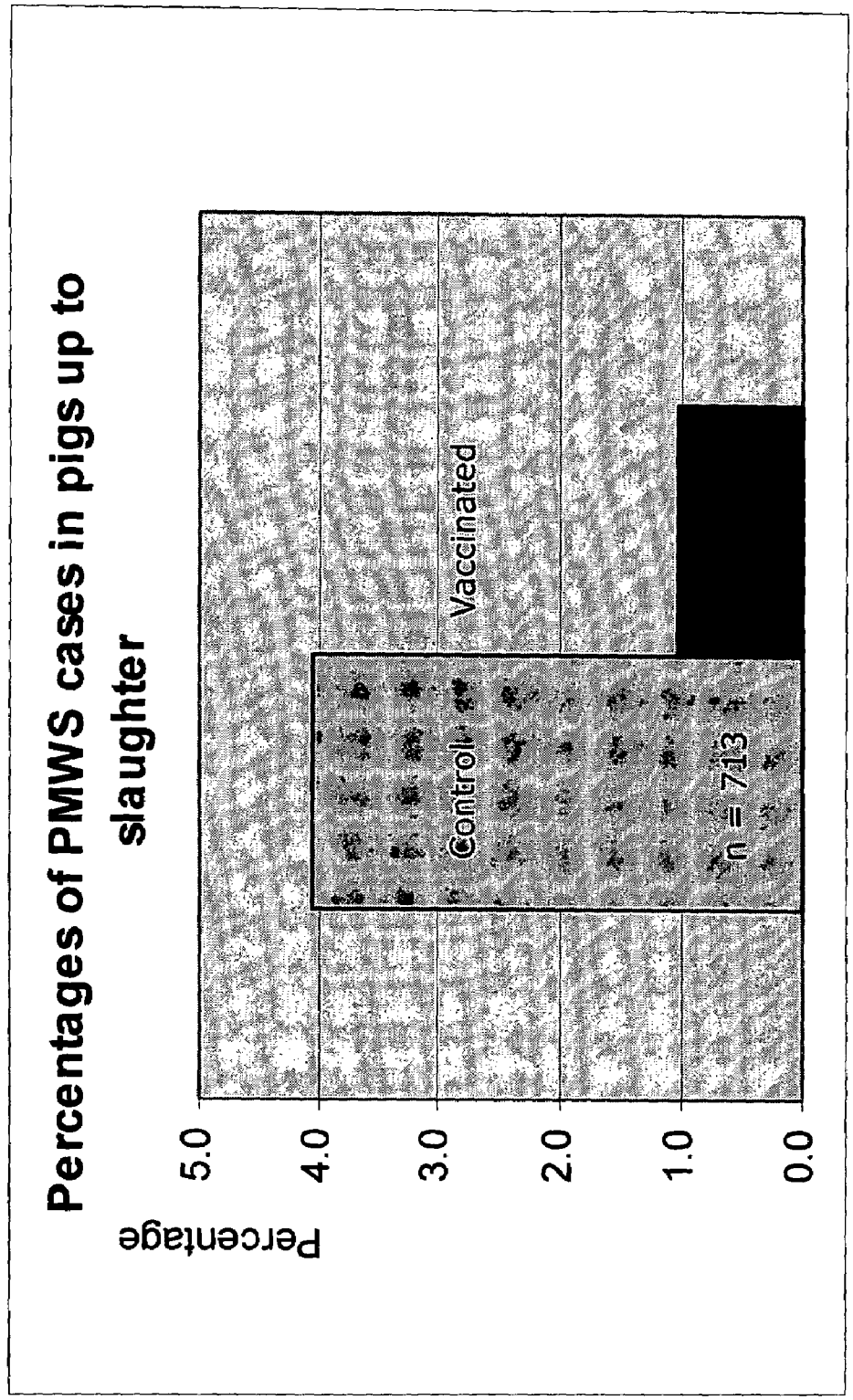
FIG. 4 depicts the results of a field efficacy trial wherein piglets (n=889 piglets) borne to sows vaccinated once before farrowing with a PCV-2 vaccine composition made according to the present invention showed a significant reduction in mortality (75% decrease) due to postweaning multisystem wasting syndrome (PMWS) as compared to control piglets (n=713) borne to unvaccinated sows.

Results: FIG. 4 shows a graph depicting the percentages of PMWS cases in piglets up to the time of slaughter. As can be seen from the graph, there was a 75% reduction in the number of cases of PMWS in piglets born to vaccinated sows as compared to the number of cases in piglets from unvaccinated controls. These results show a significant decrease in the clinical disease associated with PCV-2 infection and demonstrate the feasibility of vaccinating sows shortly before farrowing with a TS6 adjuvanted inactivated PCV2 vaccine to prevent the mortality and morbidity associated with PCV2 infection in piglets. These results further demonstrate that a significant reduction of PMWS among piglets in actual field conditions can be achieved using only one dose of a vaccine composition according to the present invention.

EXAMPLE 8

LF2 Emulsion

Using the method described above in Example 1, an oil-in-water (O/W) emulsion containing 10% oily phase.emulsion and designated as LF2 was made. The oily phase (100 ml) contained Marcol 82® 88% v/v, Span 80® 1.8% w/v and Tween 85® 10.2% w/v. The aqueous phase #1 (100 ml) contained phosphate disodic and monopotassic 0.02M isotonic buffer (pH 7.8) 88.5% v/v and 20% (w/v) solution of Tween 80® 11.5% w/v. The aqueous phase #2 (400 ml) was constituted with the phosphate disodic and monopotassic 0.02M isotonic buffer (pH 7.8), optionally containing immunogens. 100 ml of the pre-emulsion was diluted with 400 ml of the aqueous phase #2 to obtain the LF2 emulsion. The final surfactant concentration in the LF2 emulsion was 1.43% w/v. The PIT of the LF2 emulsion was >45° C., as determined by conductivity.

EXAMPLE 9

Serology Analysis after the Administration of a Swine Influenza Vaccine Adjuvanted with the LF2 Emulsion Materials and Methods: fifteen (15) piglets, about 10 weeks of age were randomly allocated into 3 groups. Group one (vaccinated) had 5 piglets vaccinated twice (on day 0 and day 28) with 2 ml of a recombinant swine influenza vaccine at 7.7 log10 $CCID_{50}$ per dose by intramuscular injection. This recombinant expression vector vaccine contained a canarypox vector encoding and expressing nucleoprotein (NP) and haemagglutinin (HA) of an H1N1 swine flu virus. The second group of 5 piglets was vaccinated twice (by intramuscular injection on day 0 and day 28) with 2 ml of the recombinant swine influenza vaccine (at 7.7 log10 $CCID_{50}$ per dose) adjuvanted with the LF2 emulsion (LF2 vaccinated group). Five piglets were left unvaccinated (control group). Blood samples were taken at D0, D14, D28, D42 and D56 post vaccination for determining haemagglutination inhibition (HI) titers.

Results: As summarized in the following table, all vaccinates showed a significant anti-swine flu antibody response from 42 to 56 days after vaccination (ANOVA, $p<0.0001$) as compared to untreated controls. However, pigs vaccinated with the LF2 adjuvanted vaccine showed a significant increase in antibody response at days 42 to 56 days post-vaccination as compared to pigs receiving the unadjuvanted recombinant vaccine (ANOVA, $p<0.0001$).

| Groups | HI (log10) | D0 | D14 | D28 | D42 | D56 |
| --- | --- | --- | --- | --- | --- | --- |
| Vaccinated | Mean | 0.9 | 0.9 | 0.9 | 1.2 | 1.2 |
|  | Std deviation | 0.00 | 0.00 | 0.00 | 0.37 | 0.21 |
| LF2 vaccinated | Mean | 0.9 | 0.9 | 0.9 | 2.04 | 1.92 |
|  | Std deviation | 0.00 | 0.00 | 0.00 | 0.33 | 0.16 |
| Controls | Mean | 0.9 | 0.9 | 0.9 | 0.9 | 0.9 |
|  | Std deviation | 0.00 | 0.00 | 0.00 | 0.00 | 0.00 |

As demonstrated by these results, the adjuvant effect of the LF2 emulsion allows the vaccine to induce a higher antibody response against the swine flu virus, as compared to the non-adjuvanted vaccine.

EXAMPLE 10

Protection Induced by a *Mannheimia Haemolytica* Vaccine Adjuvanted with the LF2 Emulsion Materials and Methods: twenty (20) calves, five months of age, negative or with low *Mannheimia haemolytica* leucotoxin antibody titers, were randomly allocated into two groups of 10 calves each. An LF2 emulsion was made as described in Example 8 above and a vaccine formulated containing inactivated *Mannheimia haemolytica* (A1 strain) at approximately 60 to 70 ELISA units (corresponding to about 0.34 mL to 1.1 mL of crude non-concentrated bacterial culture) per dose of vaccine and adjuvanted with the LF2 emulsion. One group of 10 calves was vaccinated on day 0 with 2 ml of the LF2 vaccine composition by subcutaneous injection, while the control group of 10 calves was not vaccinated. From the day of vaccination (D0) to the day of challenge (D20), all vaccinated calves were regularly examined for general and local reactions to vaccination. Clinical examination comprised an assessment of systemic reactions (such as apathy, anorexia, polypnea, salivation, trembling), recordation rectal temperature, and a measurement of local reaction at injection sites. None of the calves presented any systemic reaction to vaccination. Rectal temperatures (in ° C., mean+/−standard deviation) summarized in the following table showed a transient and slight phase of hyperthermia was observed in the vaccinated group, with a peak within 24 hours after vaccination.

|  | D0 | D0 + 4 h | D1 | D2 | D3 | D7 | D14 | D20 |
| --- | --- | --- | --- | --- | --- | --- | --- | --- |
| Vaccinated | 39.3 +/− 0.3 | 39.6 +/− 0.4 | 39.5 +/− 0.3 | 39.2 +/− 0.3 | 39.0 +/− 0.2 | 39.0 +/− 0.2 | 39.1 +/− 0.3 | 38.7 +/− 0.3 |
| Controls | 39.3 +/− 0.2 | 39.3 +/− 0.2 | 39.1 +/− 0.2 | 39.1 +/− 0.2 | 38.9 +/− 0.2 | 39.0 +/− 0.2 | 38.9 +/− 0.1 | 38.7 +/− 0.3 |

Local reactions in vaccinated calves (measured as the surface area in $cm^2$, mean+/−standard deviation) showed a strong local reaction that appeared approximately 24 to 48 hours post vaccination in all vaccinated animals and then rapidly decreased to a size of approximately 3 $cm^2$ by D14. These reactions had almost disappeared by D20. The reactions are summarized as follows:

|            | D0         | D0 + 4 h    | D1          | D2          | D3          | D7         | D14        | D20        |
|------------|------------|-------------|-------------|-------------|-------------|------------|------------|------------|
| Vaccinated | 0.9 +/− 0.4 | 9.2 +/− 12.4 | 71.3 +/− 25.8 | 72.5 +/− 29.3 | 56.9 +/− 18.0 | 15.9 +/− 8.0 | 2.6 +/− 2.6 | 2.0 +/− 1.2 |

Blood samples were obtained from all animals at various intervals (D0, D7, D14, D20 and D28) and levels of antibodies against *Mannheimia haemolytica* A1 leucotoxin performed by ELISA (titer in log10 OD50). Results showed that all calves were negative prior to vaccination. By D20, after a single vaccination, eight of the ten vaccinates had seroconverted while all control calves remained negative from D0 to D20. The ELISA results are summarized as follows:

| Groups     | ELISA (log10)      | D0    | D7    | D14   | D21   | D28  |
|------------|--------------------|-------|-------|-------|-------|------|
| Vaccinated | Mean               | <0.78 | 1.11  | 1.70  | 1.86  | 4.00 |
|            | Std deviation      | 0.00  | 0.65  | 0.90  | 0.84  | 0.26 |
| Control    | Mean               | <0.78 | <0.78 | <0.78 | <0.78 | 1.39 |
|            | Standard deviation | 0.00  | 0.00  | 0.00  | 0.00  | 1.00 |

Challenge Protocol: All calves were challenged on day 20 by intra-tracheal administration of a 30 ml challenge containing about 9.2 log10 CFU/ml (colony forming unit per milliliter) of *Mannheimia haemolytica* A1 strain. The challenge was repeated 24 hours later. From the day of challenge to the end of the study, all calves were examined daily for general clinical signs including respiratory distress. Signs monitored included general condition, anorexia, rectal temperature, nasal discharge, cough, respiratory rate, and dyspnea. Global clinical scores were calculated according to the following formula and the partial scores given in the table:

| Global clinical score = Σ (partial score × coefficient)/14 ||||
|---|---|---|---|---|
|  | 0 | 1 | 2 | Coefficient |
| General condition | Normal | Depression | Prostration | ×2 |
| Food | Normal | Reduce | Anorexia | ×3 |
| Cough | No | Intense, occasional | Weak, frequent | ×1 |
| Nasal discharge | No | Serous | Muco-purulent | ×2 |
| Respiratory rate | <35/min | 35–50/min | >50/min | ×3 |
| Rectal temperature | <39.5° C. | 39.5° C.–40.5° C. | >40.5° C. | ×3 |

For dead animals, the maximum individual daily clinical score of 2 was applied

The lung lesion scores (expressed in percentages) were also determined for each calf by using the following formula:

Lung lesion score=Σ(surface of the lesion on a lobe/surface of the whole lobe×100×*LRM*)

Wherein LRM is the lung relative mass, with a value of:
0.11 for the right cranial lobe and the right medial cranial lobe
0.07 for the right medial caudal lobe
0.35 for the right caudal lobe
0.05 for the left cranial lobe
0.06 for the left medial lobe
0.32 for the left caudal lobe, and
0.04 for the azygos lobe.

Results of challenge: Global clinical scores for each group, presented in the following table, showed that the vaccinated group demonstrated a significant reduction in global clinical scores as compared to untreated controls (p=0.046, ANOVA).

|            |                    | D20 | D21 | D22 | D23 | D24 | D25 | D26 | D27 | Cumulated score |
|------------|--------------------|-----|-----|-----|-----|-----|-----|-----|-----|-----------------|
| Vaccinated | Mean               | 0.0 | 0.7 | 0.7 | 0.6 | 0.6 | 0.5 | 0.5 | 0.5 | 4.0             |
|            | Standard deviation | 0.1 | 0.4 | 0.5 | 0.6 | 0.8 | 0.8 | 0.8 | 0.8 | 4.5             |
| Control    | Mean               | 0.1 | 0.9 | 1.1 | 1.0 | 1.1 | 1.2 | 1.2 | 1.3 | 8.0             |
|            | Standard deviation | 0.1 | 0.5 | 0.6 | 0.8 | 0.9 | 0.8 | 0.8 | 0.7 | 4.5             |

All animals that succumbed to the challenge presented with 60% or more of their lungs affected. There was a statistical tendency (p=0.08) of vaccinated animals to have fewer lung lesions than those in the control group. The number of animals per group having more than a third of their lungs affected was 2/10 (20%) for the vaccinates and 7/10 (70%) for the control animals. The number of animals having more than a third of their lungs affected was significantly lower (p=0.03, Fischer's Exact Test, one tailed) in the vaccinated group. Results of the lung lesion scores are summarized in the following table:

| Individual percentage of lung lesions in vaccinates | 74.8*<br>10.6<br>10.1<br>10.5<br>66.4*<br>6.2<br>6.9<br>32.9<br>25.4<br>8.0 | Individual percentage of lung lesions in controls | 64.5*<br>7.0<br>78.6*<br>63.1*<br>44.7<br>60.9<br>48.2<br>0.8<br>59.5*<br>32.9 |
|---|---|---|---|
| Mean +/− std deviation | 25.2 +/− 25.5 | Mean +/− std deviation | 46.0 +/− 25.5 |

*animals that succumbed to the challenge

There was a highly significant (p<0.001) and strong correlation ($R^2$=0.86) between global clinical scores and the percentage of lung lesions. Although all vaccinated animals exhibited a slight hyperthermia following vaccination, no other general reaction to vaccination was observed. Strong local reactions were observed after vaccination, but rapidly reduced to a very acceptable size and no significant lesions were observed at necropsy. These results demonstrate the safety of the vaccine adjuvanted with the LF2 emulsion.

The results of this experiment, showing that both the average clinical scores and lung lesion scores were significantly reduced in vaccinates as compared to controls, demonstrate that a single injection of the *Mannheimia haemolytica* vaccine adjuvanted with LF2 emulsion protects naïve calves against a *Mannheimia haemolytica* challenge.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A vaccine composition comprising an injectable oil-in-water (O/W) emulsion, comprising:
   (i) an aqueous solution containing at least one immunogen;
   (ii) a mineral oil;
   (iii) a non-ionic lipophilic surfactant;
   (iv) a non-ionic hydrophilic surfactant having a high hydrophilic-lipophilic balance (HLB) value of greater than 13 and less than 40; and
   (v) a non-ionic hydrophilic surfactant having a low hydrophilic-lipophilic balance (HLB) value between 9 and 13.

2. A vaccine composition comprising an injectable oil-in-water (O/W) emulsion, comprising:
   (i) an aqueous solution containing at least one immunogen,
   (ii) a paraffin oil,
   (iii) a sorbitan monooleate,
   (iv) an ethoxylated sorbitan monooleate and
   (v) an ethoxylated sorbitan trioleate.

3. The composition of claim 2, wherein the paraffin oil is present at a concentration of 29.3% v/v, the sorbitan monooleate is present at a concentration of 0.6% w/v, the ethoxylated sorbitan trioleate is present at a concentration of 3.4% w/v and the ethoxylated sorbitan monooleate is present at a concentration of 0.75% w/v.

4. The composition of claim 1, wherein the immunogen is selected from the group consisting of an inactivated pathogen, an attenuated pathogen, a subunit, a recombinant expression vector, and a plasmid or combinations thereof.

5. The composition of claim 4, wherein the immunogen is an inactivated porcine circovirus type 2 (PCV-2) virus.

6. A method for inducing an immunological response in an animal against a pathogen comprising administering to said animal a vaccine composition according to claim 4.

7. A method according to claim 6, wherein the animal is a pig, wherein the vaccine composition is administered in a single dose and wherein the administration is an intramuscular (IM) injection.

8. A vaccine composition comprising an injectable oil-in-water (O/W) emulsion, comprising:
   (i) an aqueous solution containing at least one immunogen;
   (ii) a mineral oil;
   (iii) a non-ionic lipophilic surfactant; and
   (iv) a non-ionic hydrophilic surfactant having a low hydrophilic-lipophilic balance (HLB) value between 11 and 13, said non-ionic hydrophilic surfactant is selected from the group consisting of ethoxylated fatty acid diesters of sorbitan.

9. A method for inducing an immunological response in an animal against a pathogen comprising administering to said animal a vaccine composition according to claim 1.

10. A method for inducing an immunological response in an animal against a pathogen comprising administering to said animal a vaccine composition according to claim 2.

11. A method for inducing an immunological response in an animal against a pathogen comprising administering to said animal a vaccine composition according to claim 8.

12. A method for inducing a gamma-interferon (IFNγ) response in an animal comprising administering to said animal a composition according to claim 1.

13. A method for inducing a gamma-interferon (IFNγ) response in an animal comprising administering to said animal a composition according to claim 2.

14. A method for inducing a gamma-interferon (IFNγ) response in an animal comprising administering to said animal a composition according to claim 4.

15. A method for inducing a gamma-interferon (IFNγ) response in an animal comprising administering to said animal a composition according to claim 8.

16. A method according to claim 9, wherein the animal is a pig, wherein the vaccine composition is administered in a single dose and wherein the administration is an intramuscular (IM) injection.

17. A method according to claim 10, wherein the animal is a pig, wherein the vaccine composition is administered in a single dose and wherein the administration is an intramuscular (IM) injection.

18. A method according to claim 11, wherein the animal is a pig, wherein the vaccine composition is administered in a single dose and wherein the administration is an intramuscular (IM) injection.

19. A method according to claim 12, wherein the animal is a pig, wherein the vaccine composition is administered in a single dose and wherein the administration is an intramuscular (IM) injection.

20. A method according to claim 13, wherein the animal is a pig, wherein the vaccine composition is administered in a single dose and wherein the administration is an intramuscular (IM) injection.

21. A method according to claim 14, wherein the animal is a pig, wherein the vaccine composition is administered in a single dose and wherein the administration is an intramuscular (IM) injection.

22. A method according to claim 15, wherein the animal is a pig, wherein the vaccine composition is administered in a single dose and wherein the administration is an intramuscular (IM) injection.

23. A kit having at least 2 vials, comprising: an immunogen in a first vial and an emulsion comprising an oily phase comprising a non-ionic lipophilic surfactant, a non-ionic hydrophilic surfactant having a low hydrophilic-lipophilic balance (HLB) value between 9 and 13, a mineral oil and an aqueous phase comprising a non-ionic hydrophilic surfactant having a high hydrophilic-lipophilic balance (HLB) value of greater than 13 and less than 40 in a second vial.

24. A kit having at least 2 vials, comprising: an immunogen in a first vial and an emulsion an oily phase comprising a sorbitan monooleate, an ethoxylated sorbitan trioleate, a paraffin oil and an aqueous phase comprising an ethoxylated sorbitan monooleate in a second vial.

25. A kit having at least 2 vials, comprising: an immunogen in a first vial and an emulsion comprising an oily phase comprising a sorbitan monooleate at a concentration of 1.8% w/v, an ethoxylated sorbitan trioleate at a concentration of 10.2% w/v, a paraffin oil at a concentration of 88% v/v and an aqueous phase comprising an ethoxylated sorbitan monooleate at a concentration of 2.25% w/v in a second vial.

26. The composition of claim 1, wherein the non-ionic lipophilic surfactant is present at a concentration 0.1% to 2.5% w/v.

27. The composition of claim 1, wherein the high HLB non-ionic hydrophilic surfactant is present at a concentration of 0.1% to 1.5% w/v.

28. The composition of claim 1, wherein the low HLB non-ionic hydrophilic surfactant is present at a concentration of 1% to 8% w/v.

29. The composition of claim 1, wherein the mineral oil is present at a concentration of 5% to 50% v/v.

* * * * *